US 6,629,963 B2

(12) United States Patent
Prais et al.

(10) Patent No.: US 6,629,963 B2
(45) Date of Patent: *Oct. 7, 2003

(54) SYRINGE AND NEEDLE SHIELD ASSEMBLY AND METHOD OF STERILIZING SUCH ASSEMBLY

(75) Inventors: A. Wesley Prais, Hewitt, NJ (US); Judith L. Doyle, Upper Saddle River, NJ (US); Steven L. Koziol, Columbus, NE (US); Frederic Perot, Grenoble (FR)

(73) Assignee: Becton, Dickinson and Company, Franklin Lakes, NJ (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 39 days.

(21) Appl. No.: 09/809,469

(22) Filed: Mar. 15, 2001

(65) Prior Publication Data

US 2001/0039402 A1 Nov. 8, 2001

Related U.S. Application Data

(60) Continuation-in-part of application No. 09/454,993, filed on Dec. 6, 1999, which is a continuation of application No. 09/040,067, filed on Mar. 17, 1998, now Pat. No. 6,009,933, which is a division of application No. 08/670,255, filed on Jun. 20, 1996, now Pat. No. 5,752,942.

(51) Int. Cl.[7] .............................................. A61M 5/32
(52) U.S. Cl. ...................................... 604/274; 206/365
(58) Field of Search ........................... 604/274, 164.01, 604/164.06, 164.08, 164.11, 187, 192, 264; 206/364, 365, 366; 425/73; 53/425, 426, 471, 485

(56) References Cited

U.S. PATENT DOCUMENTS 4,435,177 A  *  3/1984  Kuhlemann et al. ........ 604/263

(List continued on next page.)

FOREIGN PATENT DOCUMENTS

| DE | 4438360 | 5/1996 |
| EP | 0819442 | 1/1998 |
| EP | 0873758 | 10/1998 |
| EP | 0976415 | 2/2000 |

OTHER PUBLICATIONS

Kraton™ G2705 Polymer Compound Bulletin.
Kraton Processing Guide.
Shell Kraton Polymers for Modifications of Thermoplastic.
Kraton Polymers and Compounds Typical Properties Guide.
Application No. 09/454,993.
Application No. 09/127,524.

*Primary Examiner*—Brian L. Casler
*Assistant Examiner*—Ann Y Lam
(74) *Attorney, Agent, or Firm*—Hoffman & Baron, LLP

(57) ABSTRACT

A syringe assembly including a needle cannula having a five-beveled point and a needle shield formed of a styrene block poly(ethylene/butylene) thermoplastic elastomer which significantly reduces needle penetration force and may reduce the cycle time for gas sterilization. The multi-beveled needle cannula point includes a primary bevel, a pair of tip bevels and a pair of middle bevels each intermediate the primary bevel and a respective tip bevel, wherein the angles of rotation of the primary bevel and the intermediate bevels are substantially equal resulting in reduced heights of intercepts between the bevels, thereby reducing needle penetration force. The needle shield maintains the sharpness of the needle cannula during application, sterilization and removal of the shield and it is believed that the needle shield will also reduce the cycle time of gas sterilization as compared to rubber needle shields and vulcanizate thermoplastic elastomers.

27 Claims, 4 Drawing Sheets

U.S. PATENT DOCUMENTS

| | | |
|---|---|---|
| 4,551,138 A | 11/1985 | Shinohara .................... 604/262 |
| 4,561,445 A * | 12/1985 | Berke et al. ................. 128/642 |
| 4,964,866 A | 10/1990 | Szwarc |
| 4,986,818 A | 1/1991 | Imbert et al. |
| D322,671 S | 12/1991 | Szwarc |
| D332,308 S | 1/1993 | Imbert et al. |
| 5,752,942 A | 5/1998 | Doyle et al. |
| 5,807,343 A * | 9/1998 | Tucker et al. ................ 604/187 |
| 5,858,008 A * | 1/1999 | Capaccio .................... 604/263 |
| 5,911,711 A | 6/1999 | Pelkey |
| 5,958,317 A * | 9/1999 | Aguadisch et al. ......... 264/159 |
| 6,009,933 A | 1/2000 | Doyle et al. |
| 6,013,723 A * | 1/2000 | Akao ......................... 524/577 |
| 6,171,283 B1 | 1/2001 | Perez et al. |

\* cited by examiner

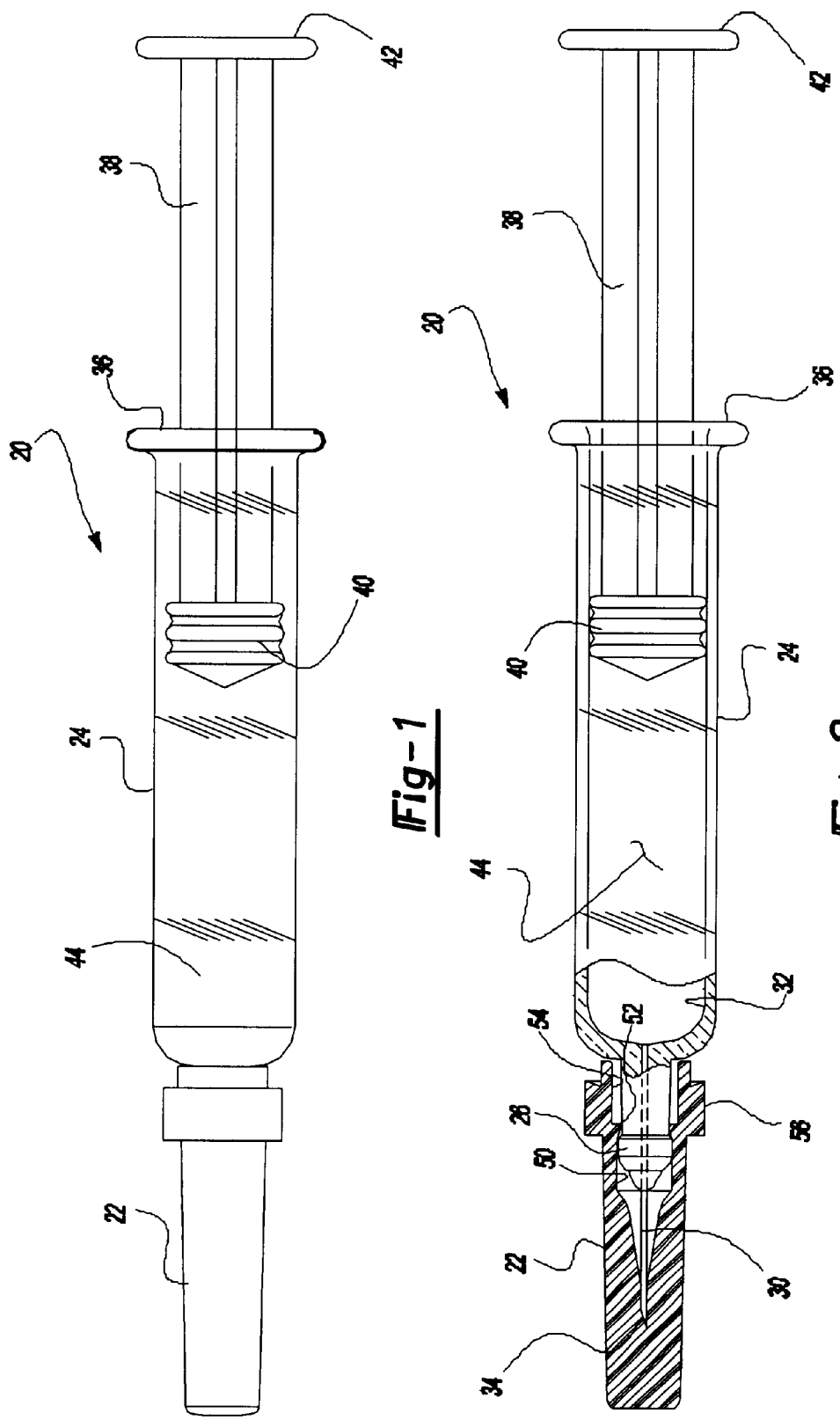

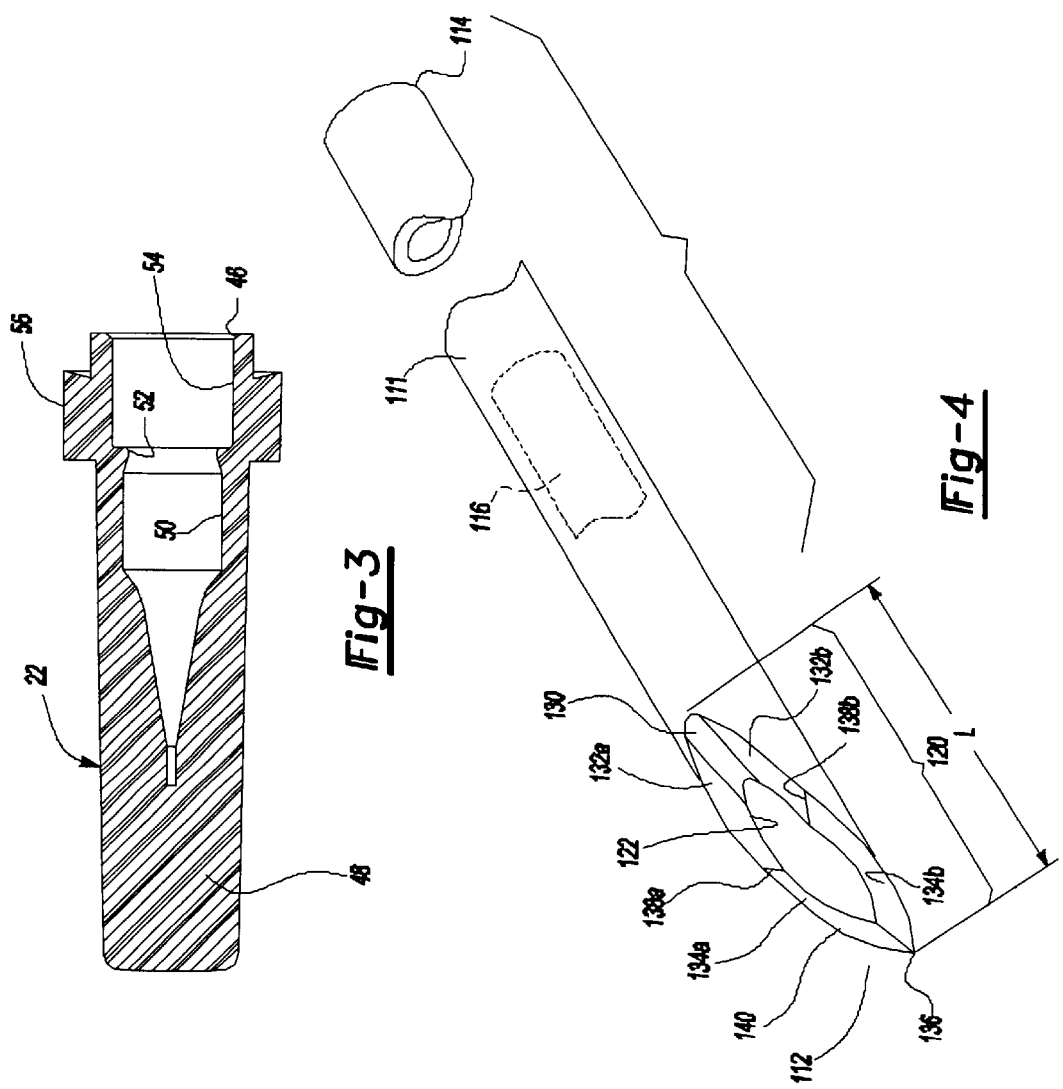

SYRINGE AND NEEDLE SHIELD ASSEMBLY AND METHOD OF STERILIZING SUCH ASSEMBLY

RELATED APPLICATIONS

This application is a continuation in part application of Ser. No. 09/454,993, of Dec. 6, 1999, which application was a continuation of Ser. No. 09/040,067, filed Mar. 17, 1998, now U.S. Pat. No. 6,009,933, which application was a divisional application of Ser. No. 08/670,255, filed Jun. 20, 1996, now U.S. Pat. No. 5,752,942.

FIELD OF THE INVENTION

The present invention relates to hypodermic syringes, particularly sterilized prefilled or prefillable syringes, having a needle shield or sheath providing reduced needle penetration force, a method of making a sterilized syringe assembly and an improved multibeveled needle tip configuration.

BACKGROUND OF THE INVENTION

A hypodermic syringe typically includes a generally tubular barrel portion, which may be formed of glass or plastic, a plunger having a stopper typically formed of an elastomeric material, such as rubber or synthetic rubber, and a needle cannula typically formed from an elongated tube having a fluid-conducting lumen. Such syringes may be prefilled with a medicament, drug or vaccine which require a shield or sheath enclosing the sharp end of the needle cannula typically formed of rubber or synthetic rubber. A needle shield includes an open end, a closed end, and a needle passage through the open end which receives the sharp end of the syringe needle cannula. As will be understood, hypodermic syringes must be sterilized prior to use by the healthcare worker or patient and such syringes are typically sterilized by the manufacturer and generally sealed in a plastic container ready for use.

A preferred method of sterilizing hypodermic syringes, particularly prefillable or prefilled syringes, is to "immerse" the syringe assembly in a sterilizing gas, such as ethylene oxide. Although there are several industry recognized methods of gas sterilization, such methods depend upon permeation of the sterilization gas into the passage of the needle shield to sterilize the syringe needle cannula. However, natural and synthetic rubber and vulcanizate thermoplastic elastomers are characterized as having a low gas permeability. Further, ethylene oxide gas, which is commonly used for gas sterilization. Alternatively, steam sterilization may also be used, but is generally limited to subsequent or "terminal" sterilization. As used herein, "sterilization gas" may be any gas used for sterilization, including ethylene oxide and steam. Therefore, the cycle time required for gas sterilization is relatively long. That is, the syringe is first immersed in the sterilization gas for a time sufficient for the gas to sterilize the syringe, including the needle cannula. Following sterilization, the sterilized syringes are "quarantined" for a time sufficient for the sterilization gas to escape, including any residual gas trapped in the needle shield. Thus, the sterilization cycle time is dependent in part upon how easily the gas penetrates through the needle shield during sterilization and removal of the gas from the syringe assembly. Tests are conducted to confirm that the sterilized syringe assemblies contain only minute traces of residual ethylene oxide or water in steam sterilization prior to release for distribution or sale.

A particular concern with the design of syringes is reduction of the needle cannula penetration force and patient comfort. The distal end or point of the needle cannula is typically provided with a tip geometry for piercing a patient's epidermis, flesh or tissue to deliver a fluid medicament, drug or vaccine stored or held in the syringe barrel. A healthcare worker or patient may also employ the syringe needle cannula to pierce an elastomeric septum or stopper of a vessel, such as a vial, to reconstitute dry or powdered medicament, drug or vaccine or to aspirate a liquid medicament, drug or vaccine contained in the vial.

Various considerations must be made when designing a syringe. For example, it is obviously desirable to minimize the needle cannula penetration force necessary for urging the needle cannula point or tip through the epidermis and flesh of the patient. It is generally believed that by reducing the needle cannula penetration force, the patient will perceive less pain. Another consideration in designing needle cannula point geometry is to prevent or minimize "coring." Coring, as those skilled in this art understand, results when a portion of the material through which the needle cannula has penetrated becomes lodged in the lumen adjacent the needle cannula tip.

Various attempts have been made to reduce the required penetration force of syringe needle cannulas and reduce coring as discussed more fully in the above-referenced co-pending application. These efforts have been primarily directed to improving the design of the needle cannula tip by providing facets or bevels, for example, to reduce the required penetration force. Other attempts have been made to minimize the required penetration force by minimizing coring. However, these efforts have not been as successful as desired. Further, various efforts have been made to improve syringe needle cannula shields or sheaths, particularly for prefilled hypodermic syringes. Such improvements generally relate to protecting the needle cannula and preventing inadvertent coring of the needle shield by the needle cannula as disclosed, for example, in U.S. Pat. No. 4,964,866 assigned to the assignee of the present application, the disclosure of which is incorporated herein by reference. Further efforts have been made in the design of needle shields or syringes to reduce the gas sterilization cycle time by providing non-linear channels in the needle cannula shield which permit entry and egress of the sterilization gas while preventing entry of microorganisms.

However, no one has recognized the inter-relation between the selection of the material from which the needle shield is formed and the required penetration force of the needle cannula. The present invention relates to an improved five-beveled point geometry for a hypodermic needle and a needle shield which reduces the penetration force of the needle cannula. It is also believed that the improved needle shield will reduce gas sterilization cycle time.

SUMMARY OF THE INVENTION

The syringe assembly of this invention utilizes an improved five-bevel needle configuration which reduces penetration force and a needle cannula shield or sheath formed of a styrene block thermoplastic elastomer which maintains the sharpness of the needle cannula during application, sterilization and removal of the shield, and may reduce the cycle time of gas sterilization. As described above, the improved five-beveled needle cannula configuration and needle shield may be utilized with any conventional injection device, including a conventional prefilled hypodermic syringe, and the improved needle shield or sheath of this invention has further advantages when the syringe assembly is gas sterilized. A conventional syringe assembly includes a generally tubular barrel, typically made of glass, but which may also be formed from various polymers, a needle cannula fixed to the tip portion of the barrel having a lumen therethrough in fluid communication with the interior of the barrel portion and syringes. Prefillable and prefilled syringes include a needle shield having an open end and a needle passage through the open end which receives the sharp distal end of the needle cannula to protect the needle cannula and prevent loss of fluid in the syringe barrel. The needle cannula is typically formed of stainless steel, such as AISI 304, and the needle cannula is generally coated with a lubricant, such as a silicone oil. U.S. Pat. No. 5,911,711 assigned to the assignee of this application discloses preferred needle lubricants. The needle shield or sheath is typically formed of a natural or synthetic rubber generally including a significant amount of a filler to improve the mechanical properties and reduce cost. More recently, with the advent of thermoplastic elastomers replacing rubber and synthetic rubber polymers in various applications, the prior art has suggested the use of thermoplastic elastomers for syringe tip shields and tip caps. However, as set forth below, most thermoplastic elastomers provide little if any advantage over natural or synthetic rubber and vulcanizate thermoplastic elastomers suffer other disadvantages, including shrinkage during molding, lack of dimensional stability and coring. There is, therefore, a need for an improved needle cannula point configuration which reduces penetration force and a needle shield which protects and maintains the sharpness of the needle cannula point.

It is believed by the inventors that a primary reason that a patient experiences pain when a needle cannula penetrates the skin or flesh of the patient, the needle point catches on the skin or flesh as the needle penetrates. One cause of a needle point catching on the skin or flesh is believed to be due to the height of the "intersect" established at the transition between differing bevels forming the needle point. It is believed that if this transition between differing bevels forming the needle point is less pronounced, the height of the intersects would be reduced. The effect of reducing the heights of the transitions would be to approximate, from a series of bevels forming the cannula needle point, a more continuous, unitary bevel face. The resulting continuing bevel point would thus require less penetration force in entering a patient's skin and flesh. By reducing penetration force, it is believed that the patient will also experience less pain.

Accordingly, one aspect of this invention relates to a multi-beveled needle point, reducing the heights of the intersects created between merging bevels that results in a more continuous bevel face. As described above, a needle cannula has a central lumen defining an axis through the needle cannula. The multi-beveled cannula needle point defines an opening to the lumen for the passage of fluids between a medical delivery device, such as a syringe, and a patient or vessel. The multi-beveled point preferably includes a primary bevel, a pair of tip bevels, and a pair of middle bevels. Each of the middle bevels are contiguous with the primary bevel, and meet a respective one of the tip bevels at an intersect. The primary bevel is formed or otherwise provided on the cannula by inclining the central axis of the needle cannula to a first planar angle respective of a reference plane.

The needle point, formed of five distinct bevels, displays reduced height intersects, resulting in a more continuous bevel face about the opening. It is believed that by providing a series of five distinct bevels, the needle point is lengthened over the needle points conventionally in use, and owing to the reduced height intervals, results in an effective outer diameter at the needle point less than the outer diameter of the needle points currently in use, all of which contribute to reduced needle penetration force.

The needle shield of this invention is formed of a styrene block thermoplastic elastomer, most preferably a styrene block(polyethylene/butylene) thermoplastic elastomer having a Shore A hardness of between 30 and 90 or more preferably between 45 and 65. The needle shield includes an open end and a passage through the open end configured to receive the needle cannula and preferably encloses the entire needle cannula and a portion of the syringe tip to fully protect the cannula and prevent entry of microorganisms following sterilization. In the most preferred embodiment, the internal passage includes an integral annular rib, adjacent the open end, which assures retention of the needle shield on the syringe tip portion and the needle shield is preferably enclosed by a rigid cover or shield.

As discussed in more detail hereinbelow, the needle shield of this invention has several unanticipated and unexpected advantages over needle shields formed of natural or synthetic rubber or conventional vulcanizate thermoplastic elastomers. First, extensive bench and clinical testing has established that a needle cannula shield formed of a styrene block thermoplastic elastomer, particularly a styrene block poly (ethylene/butylene) thermoplastic elastomer maintains the sharpness of the needle cannula, particularly the needle cannula point, during application and removal of the needle shield as compared to natural rubber or synthetic rubber needle shields and conventional vulcanizate thermoplastic elastomers. This improvement results in reduced penetration force which is now believed to result from at least two factors which were discovered during clinical trials and bench testing. First, the needle cannula of a hypodermic syringe is conventionally coated with a medical grade lubricant, such as a silicone oil lubricant, to reduce penetration force. It is now believed that a conventional needle shield wipes away the lubricant on the needle cannula, particularly at the needle point, which is important to reduction of penetration force. As set forth above, a conventional needle shield includes a passage configured to receive the needle cannula and most preferably includes a small bore which closely receives the needle point. Thus, the lubricant may be wiped away during the receipt and removal of the needle shield on the needle cannula. This was confirmed by electron microscopic examination of the needle cannula following insertion of the needle cannula in the needle shield and removal of the needle shield from the needle cannula. The lubricant may also be absorbed by the needle shield, particularly natural and synthetic rubber needle shields having a high filler content. Second, needle shields formed of natural or synthetic rubber having a high filler content are abrasive, which may result in microabrasion of the needle point reducing the sharpness of the needle. Regardless of the cause, however, bench and clinical testing has established that use of a needle shield formed of a styrene block poly(ethylene/butylene) thermoplastic elastomer results in less penetration force and improved sharpness as perceived by healthcare workers making the injections. This improvement was unexpected.

Another potential advantage of a needle shield formed of a styrene block thermoplastic elastomer, particularly a styrene block poly(ethylene/butylene) thermoplastic elastomer, is reduced at sterilization cycle time. As set forth above, syringe assemblies are conventionally sterilized with ethylene oxide gas, which is toxic. During sterilization, the syringe assembly is flooded or "immersed" in the ethylene oxide gas or other sterilization gas including steam by one of several known methods. As will be understood, the sterilization gas must "penetrate" the needle shield to sterilize the needle cannula. However, rubber and conventional vulcanizate thermoplastic elastomers are characterized as having a low gas permeability, resulting in slow transmission of the sterilization gas into the passage in the needle shield containing the needle cannula. Further, because ethylene oxide gas is toxic, all of the sterilization gas must be removed from the needle shield before packaging. Again, because of the slow transmission of the sterilization gas out through the needle shield, the syringe assembly is quarantined until substantially all of the sterilization gas permeates out through the shield. Unexpectedly, a styrene block poly (ethylene butylene) thermoplastic elastomer has a relatively high gas permeability to ethylene oxide gas as established by testing for residual gas in the shield following sterilization.

The most preferred embodiment of the needle shield for a syringe needle cannula of this invention is formed of a styrene block poly(ethylene/butylene) thermoplastic elastomer having a Shore hardness of between 45 and 65. The most preferred composition for the needle shield of this invention also includes about one to three percent colorant which contains carbon black to improve structural integrity and reduce coring.

Other advantages and meritorious features of the syringe assembly of this invention will be more fully understood from the following description of the preferred embodiments, the appended claims, and the drawings, a brief description of which follows.

BRIEF DESCRIPTION OF THE DRAWINGS

FIG. 1 is a side view of a syringe having the improved needle shield and needle cannula point configuration of this invention;

FIG. 2 is a partially cross-sectioned view of FIG. 1;

FIG. 3 is an enlarged side cross-sectional view of the needle shield shown in FIGS. 1 and 2;

FIG. 4 is a frontal perspective view of a multi-beveled needle tip geometry in accordance with the present invention;

DETAILED DESCRIPTION OF THE PREFERRED EMBODIMENTS

Figure 5:
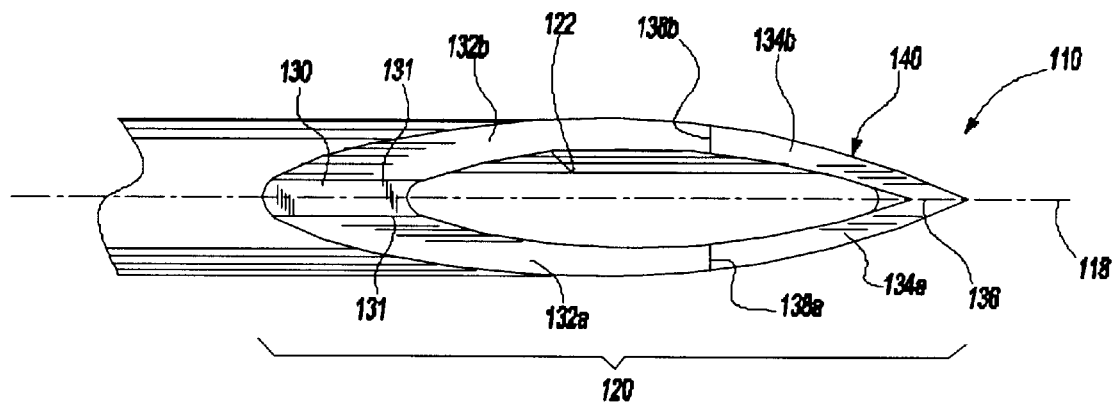
FIG. 5 is a top view of the multi-beveled needle tip of FIG. 4.

The syringe assembly 20 illustrated in FIGS. 1 and 2 and the needle shield or sheath illustrated in FIGS. 2 and 3 may be generally conventional in configuration except as described below and may take various forms within the purview of the appended claims. That is, the syringe assembly 20 may be any conventional injection device, such as the syringe assembly disclosed having a generally tubular barrel portion 24 including a reduced diameter tip portion 26 and a needle cannula 30 affixed by any suitable means to the tip portion 26 of the barrel, such that the lumen through the needle cannula is in fluid communication with the interior 32 of the barrel. The barrel 24 is typically formed of glass, but may also be formed of a suitable plastic, and the needle cannula 30 is typically formed of stainless steel. The sharp tip 34 of the needle cannula preferably includes a five-beveled point as shown in FIGS. 4–9 and described below.

The barrel 24 typically includes a radial flange 36 at its open end which receives a stopper assembly, including a plunger rod 38 and a stopper 40 generally formed of an elastomeric material, such as natural rubber or synthetic rubber. The resilient stopper 40 may be connected by any suitable means to the plunger rod 38, including a threaded connection (not shown). As will be understood by those skilled in this art, the resilient stopper 40 forms an interference sealed fit with the interior surface 32 of the barrel such that as the plunger 40 is reciprocated through the barrel, a medicament, drug or vaccine may be aspirated from a vial, for example, or a medicament, drug or vaccine 44 may be injected into a patient. However, the most preferred embodiment of this invention is a prefilled syringe for medical injections. The plunger rod 38 may also include a radial flange 42 as shown to assist the patient or healthcare worker during use of the syringe assembly 20. As set forth herein, the needle shield 22 of this invention is particularly suitable for sterilization of prefillable or prefilled syringe assemblies.

FIG. 3 is an enlarged cross-sectional view of the needle shield 22 shown in FIGS. 1 and 2. The needle shield includes an open end 46 which may be slightly tapered or conical as shown to receive the barrel tip portion 26 of the barrel as shown in FIG. 2. The needle shield includes a closed end portion 48 and a needle passage 50 through the open end 46 with the needle passage 50 having an inner wall 51 which seals against the tip portion 26 of the syringe. In this preferred embodiment, the needle passage 50 includes an internal rib 52 which is received in a reduced diameter portion of the tip portion 26 of the syringe barrel as shown in FIG. 2 to assure retention of the shield on the syringe. The needle passage also includes a reduced diameter cylindrical portion 54 adjacent the internal rib 52 which assists in retaining the needle shield on the tip portion of the syringe to avoid the needle shield popping off, especially during sterilization. The annular internal rib 52 maybe continuous or interrupted to assist in removal from the mold. This embodiment also includes an external annular rib or flange 56, adjacent the open end, which is adapted to receive and retain a rigid tubular shield which may be used to enclose the shield 22 as disclosed in the above referenced U.S. Pat. No. 4,964,866.

As set forth above, the needle shield 22 of this invention is formed of a styrene block thermoplastic elastomer, preferably a styrene block poly(ethylene/butylene) thermoplastic polymeric elastomer having a Shore A hardness of between 30 and 90, most preferably between 45 and 65. A needle shield formed of this thermoplastic elastomer has several important and unexpected advantages over conventional rubber shields and shields formed of conventional vulcanizate thermoplastic elastomers. One very important advantage of a syringe assembly having a needle shield formed of a styrene block poly(ethylene/butylene) thermoplastic polymeric elastomer is reduced needle penetration force as established by bench testing and clinical trials as follows. Three variables were tested by the applicant as part of a major program to reduce the penetration force of syringe needles and improve patient comfort during injections. These variables included a comparison of (1) the five-bevel needle point design disclosed herein and a standard three-bevel design, (2) needle lubricant (which is an aminofunctional polydimethylsiloxane copolymer available from Dow Corning) and the conventional silicone lubricant, and (3) a needle shield formed of a styrene block poly(ethylene/butylene) thermoplastic polymeric elastomer having Shore A hardness of between 45 and 65 and a conventional needle shield formed of rubber. Previous bench testing showed no improvement in penetration force between sterilized syringes having a rubber needle shield and a needle shield formed of a conventional vulcanizate thermoplastic elastomer, namely Santoprene® of Advanced Elastomer Systems of Akron, Ohio. Santoprene® is a polypropylene ethylene-propylene terpolymer rubber-based vulcanizate. The needle shield formed of a styrene block poly(ethylene/butylene) thermoplastic polymeric elastomer was KRATON® G 2705 available from Kraton Company of Houston, Tex. Other needle shields formed of other thermoplastic elastomers were also molded; however, various problems were encountered during molding, including shrinkage, cracking, etc. KRATON® polymers are available from Kraton Company in linear, diblock, triblock and radial polymers. Each molecule of KRATON® polymers consists of block segments of styrene monomer units and rubber monomer units. Each block's segment may consist of 100 monomer units or more. The most common structures of the KRATON® polymers are the linear A-B-A block types: styrene-butadiene-styrene (SBS), styrene-isoprene-styrene (SIS). However, the KRATON® G series polymers, are specialized polymers of the radial $(A-B)_N$ type and the most preferred thermoplastic elastomer for this application is KRATON® G polymer series, which is a polystyrene block poly(ethylene/butylene) thermoplastic elastomer. The KRATON® G 2705 polymer is also FDA approved for contact with foods. Of all of the variables tested, the most significant improvement in penetration force verified by bench testing and reduced pain resulting from simulated injections verified by clinical testing, the most significant improvement was found with needle shields formed of a styrene block poly (ethylene/butylene) thermoplastic polymeric elastomer, such as KRATON® G 2705, as discussed below.

The applicant conducted a fall 16-week bench study comparing penetration forces of syringes having needle shields formed of natural rubber and Santoprene® which, as stated above, is a polystyrene EPDM-based vulcanizate thermoplastic elastomer available from Advanced Elastomer Systems. The study also included standard methods for accelerated aging for five years. All of the syringes tested were sterilized by standard procedures with ethylene oxide and part of the group of each syringe type in the evaluation were subsequently steam sterilized using established parameters to simulate "terminal" sterilization. These bench tests determined that there was no difference within normal statistical variations between the penetration forces of syringes having needle shields formed of Santoprene® thermoplastic elastomers and natural rubber. The natural rubber needle shields were formed of one of the common formulations of commercially available natural rubber used for needle shields.

The applicant also conducted bench tests comparing penetration forces of syringes having needle shields formed of natural rubber and a styrene block poly(ethylene/butylene) thermoplastic elastomer (KRATON® G 2705). This was a 16-week study with conventional syringes including needle cannulas having conventional 23 gauge needle cannulas with three bevel points and the needle cannulas were coated with conventional silicone lubricant. In surrogate tissue, the peak penetration force of syringes having needle shields formed of a styrene block poly(ethylene/butylene) thermoplastic elastomer (KRATON® G 2705) compared to natural rubber needle shields following sterilization by ethylene oxide was reduced 16% following sterilization with ethylene oxide plus terminal steam sterilization. Bench testing in Faultless Vial Stoppers (FVST) of Abbott Laboratories, the force reduction was 5% in both cases, consistent with earlier results. Testing after eight weeks of aging showed similar trends and after 16 weeks of aging, the trend continued strongly. In surrogate tissue, the peak force was reduced by 11% with needle shields formed of styrene block poly (ethylene/butylene) thermoplastic elastomer compared to natural rubber where the samples were sterilized with ethylene oxide and 9.5% when the samples were sterilized with ethylene oxide plus terminal steam sterilization. The following table summarizes these results.

| Peak penetration force test results, grams (SD = standard deviation) | | | | | | |
|---|---|---|---|---|---|---|
| Human skin substitute: | | | | | | |
| NS | T = 0 | T = 0 | T = 8 wks. | T = 8 wks. | T = 16 wks. | T = 16 wks. |
| Material: | EtO only | EtO & T.S. | @ 60° C. EtO only | @ 60° C. EtO & TS. | @ 60° C. EtO only | @ 60° C. EtO & T.S. |
| Natural Rubber | 204.50 SD = 27.96 | 220.49 SD = 27.08 | 197.25 SD = 29.20 | 206.99 SD = 32.00 | 219.68 SD = 52.22 | 200.27 SD = 29.95 |
| Kraton G2705 | 183.75 SD = 34.49 | 185.05 SD = 25.41 | 159.67 SD = 15.37 | 175.24 SD = 17.95 | 157.78 SD = 28.89 | 170.86 SD = 24.77 |

Faultless gray rubber vial stopper:

| NS Material: | T = 0 EtO only | T = 0 EtO & T.S. | T = 8 wks. @ 60° C. EtO only | T = 8 wks. @ 60° C. EtO & T.S. | T = 16 wks. @ 60° C. EtO only | T = 16 wks. @ 60° C. EtO & T.S. |
|---|---|---|---|---|---|---|
| Natural Rubber | 471.24 SD = 38.25 | 464.97 SD = 76.15 | 521.97 SD = 32.14 | 530.74 SD = 34.5 | 592.98 SD = 121.3 | 543.13 SD = 42.10 |
| Kraton G2705 | 453.89 SD = 28.28 | 443.02 SD = 33.65 | 509.88 SD = 37.26 | 509.63 SD = 31.43 | 483.02 SD = 27.71 | 511.13 SD = 51.57 |

Clinical tests were also conducted by the applicant with prefillable syringe systems commercially available from the applicant. As set forth above, these clinical trial were conducted to test three components of syringes, namely needle point configurations (3 vrs. 5 beveled needle points), needle lubricants and needle shields formed of natural rubber and styrene block (polyethylene/butylene) thermoplastic elastomer (KRATON® G 2705) to determine whether there was any significant difference in either perceived pain or ease of penetration. The tests were conducted with 25 gauge, 16.7 mm. (⅝") HYPAK® cannula needles. The needles were used for both subcutaneous (SC) and intramuscular (IM) injections. Although no significant difference was found in either pain or ease of penetration between three and five-beveled needles with intramuscular injections, there was a significant improvement in ease of penetration scores (assessed by nurses) with subcutaneous injections using the five-bevel needle design disclosed herein. Further, previous bench and clinical testing determined that 27 gauge needle cannulas having the improved five-bevel design resulted in a 15% to 18% reduction in penetration force in human skin substitute as compared to conventional needle cannulas of the applicant having three bevels.

In the second clinical study conducted by the applicant, 12 nurses and 14 subjects per nurse (168 subjects total) participated in a clinical trial to evaluate three factors with respect to pain, sharpness, and a general feeling of a particular injection. Only nurses who demonstrated sensitivity to differences in needle performance were chosen for this study. Each subject received four subcutaneous injections in the arm, alternating between the arms. Subjects received only needle sticks, not actual injections from a syringe with no stopper or plunger. The three factors studied (point configuration, lubrication and shield material) were crossed to create eight treatment combinations. The randomization schedule accounted for blocking due to nurse, subject within nurse, order of injection and side injection. Sharpness, as perceived by the nurse, was measured on a visual analog scale (VAS), and ranges from zero (excellent sharpness) to 100 (dull) as perceived by the nurse was recorded. Each sharpness VAS entry was measured by two different people, with the average measurement being used for the data analysis. The feeling of the injection as perceived by the nurse was qualified with five integer scale response variables. The overall feel of the injection was rated on a 13-point scale. The initial resistance, smoothness of penetration and roughness/shatters/ripping response variables were measured on a 4-point scale. In addition, each of the five responsible variables was oriented such that the lower scores were the preferred scores regarding product performance. Finally, the nurses made an overall clinical acceptability assessment for each "injection." "Initial resistance" was described as what was felt as the needle starts to puncture the skin and breaks through the epidermis layer (striatum corneum). The data from these tests regarding initial resistance established that a syringe having a needle cannula with a five-bevel configuration and a needle shield formed of a styrene block poly(ethylene/butylene) thermoplastic elastomer had the least initial resistance and syringes having a three-beveled point with a needle shield formed of a styrene block poly(ethylene/butylene) thermoplastic elastomer was second best. Syringes having needle shields formed of rubber received poor performance ratings.

"Smoothness in penetration" describes whether the patient or nurse perceived an increase in pressure at any point during the injection process going in or during withdrawal. For going in, syringes having a three-beveled point with a styrene block poly(ethylene/butylene) thermoplastic elastomer was found clear-cut best. Syringes having a five-beveled point and a needle shield formed of a styrene block poly(ethylene/butylene) thermoplastic elastomer were found second best. Again, the syringes having needle shields formed of rubber had the poorest ratings. For withdrawal, no significant difference was found between the type of needle cannula or lubricant, but needle shields formed of a styrene block poly(ethylene/butylene) thermoplastic elastomer was found preferable to syringes having rubber needle shields.

Finally, pain as perceived by the subject, was measured on a visual analog scale (VAS) ranging from zero (no pain) to 100 (very severe pain). Each pain VAS entry was measured by two different people, with the average measurement being used for the data analysis. Pain was also measured with the Gracely scale, and integer-valued scale that ranges from zero to 20. Although there was no statistically significant difference in pain perception between the treatment groups, the treatment groups where the injection was made with syringes having a needle shield formed of a styrene block poly(ethylene/butylene) thermoplastic elastomer were perceived by the nurse as having a 50% improvement in sharpness and almost 30% less perceived pain by the patient compared to conventional syringes having a rubber needle shield.

On the basis of this clinical study, the applicant determined that the primary improvement in perceived sharpness and reduced pain resulted from the substitution of a needle shield formed of a styrene block poly(ethylene/butylene) thermoplastic elastomer (KRATON® G 2705) for a natural rubber shield. No significant difference in these tests were found with changes of the needle lubricant. Needle shield removal testing also established that a needle shield formed of a styrene block poly(ethylene/butylene) thermoplastic elastomer with about one to three percent by weight colorant including carbon black maintained a range of removal forces from the syringe barrel tip that were acceptable as compared to the control. There were no separation failures of the samples with styrene block poly(ethylene/butylene) thermoplastic elastomers.

The addition of up to about two percent by weight of colorant including carbon black was found to reduce needle coring by about 80%. Colorant including Carbon black was added to the styrene block thermoplastic elastomer (KRATON® G 2705) in a ratio of 50 to one or 2% colorant. The colorant included about ⅔ styrene based resin carrier, such that the carbon black content was about ⅓ of the content of the colorant or about 0.66% of the thermoplastic elastomer. The carbon black colorant used was UNOO55P from Clariant Company at Holden, Mass. Tests conducted of needle shields having about four percent of colorant including carbon black did not reduce coring as well. Thus, the most preferred composition of the needle shield includes about one to three percent carbon black colorant.

The improved results with needle shields formed of a styrene block poly(ethylene/butylene) thermoplastic elastomer is not fully understood. It is believed, however, that rubber shields either wipe away or absorb the needle lubricant, resulting in greater perceived pain. This belief was confirmed by microscopic examination of the needle point, wherein needle lubricant was observed on needle points which were enclosed with a needle shield formed of a styrene block poly(ethylene/butylene) thermoplastic elastomer (KRATON® G 2705) and no lubricant was observed on needle points which were enclosed by rubber needle shields. Another possibility is that the filler used in conventional rubber formulations is abrasive, resulting in abrasion of the needle point and increased pain. Thus, while the needle point configuration and lubricant were not deemed to be statistically significant in such clinical trial, the significance of the needle point configuration may have been masked in these tests.

The applicants believe that another advantage of syringes having needle shields formed of a styrene block poly(ethylene/butylene) thermoplastic elastomer will be improved gas permeability over rubber needle shields and shields formed of vulcanizate thermoplastic elastomers such as Santoprene®. As set forth above, hypodermic syringe assemblies including prefilled syringes must be sterilized before use. Typically, hypodermic syringes are sterilized by immersion in ethylene oxide or steam as described above. However, because ethylene oxide gas is toxic, the gas must be removed prior to packaging. Rubber and other vulcanizate thermoplastic elastomers, such as Santoprene,® are reported to have a low gas permeability. Although no ethylene oxide gas permeability comparisons are readily available for ethylene oxide gas, the applicant compared ethylene oxide gas residuals between needle shields formed of a styrene block poly(ethylene/butylene) thermoplastic elastomer having up to one percent carbon black (KRATON® G 2705) and a blend of natural rubber and styrene butadiene rubber. These tests were conducted by immersion of the syringe assemblies in purified water after sterilization with ethylene oxide gas with a needle shield with and without a rigid needle shield guard as disclosed in the above referenced U.S. patent. The following table summaries the test results, wherein the ethylene oxide (EtO) gas residuals for the simulation of use for the KRATON® G 2705 needle shields were below the limit of 0.4 µg/ml and the ethylene chlorydrine residuals were below the limit of 12.5 µg/ml. Thus, the results were better for needle shields formed of a styrene block poly(ethylene/butylene) thermoplastic elastomer than a rubber blend of natural and synthetic shields.

|  | 1 EtO Cycle | | 2 EtO Cycles | |
|---|---|---|---|---|
|  | Rubber Blend | RNS TPE | Rubber Blend | RNS TPE |
| Test by simulation of use | No detection | No detection | 3.5 µg/ml | 0.1 µg/ml |
| Test by immersion without the plastic rigid shield | 1.8 µg/g | 0.3 µg/g | 3.0 µg/g | 2.0 µg/g |
| Test by immersion with the plastic rigid shield | 1.9 µg/g | 1.3 µg/g | 2.7 µg/g | 1.7 µg/g |

Based upon this test, the applicant believes that the improved gas permeability of needle shields formed of styrene block poly(ethylene/butylene) thermoplastic elastomers will reduce gas sterilization cycle time over rubber needle shields and shields formed of vulcanizate thermoplastic elastomers including Santoprene® and reduce ethylene oxide gas residuals following sterilization.

In the following description of FIGS. 4 to 9, the term "proximal" denotes a direction closest to a practitioner, while the term "distal" denotes a direction furthest from a practitioner. FIGS. 4 to 9 depict a hypodermic needle 110 characterized by a multi-beveled point 120 in accordance with the present invention. As the skilled artisan will appreciate, hypodermic needle 110 can be formed from a tube or cannula 111 defining therein a fluid carrying duct or lumen 116. Hypodermic needle 110 includes a proximal end 114 which can be attached in fluid communication with a medical delivery instrument, such as the syringe shown in FIGS. 1 and 2. Multi-beveled point 120 defines a fluid opening 122 for passage of fluids to and from fluid carrying lumen 116. The fluid carrying lumen is characterized by a central axis 118.

Multi-beveled point 120 is characterized by a length "L" and is formed through a plurality of individual bevels that together define a beveled face 140 about the periphery of fluid opening 122. In the embodiment disclosed by applicants herein, the multi-beveled point is characterized by a primary bevel 130; a pair of middle bevels 132a, 132b; and a pair of tip bevels 134a, 134b. Each of the pair of middle bevels 132a, 132b and each of the pair of tip bevels 134a, 134b are substantially symmetrically formed on opposite sides of primary bevel 130, as will be further described hereinbelow. Adjacent middle and tip bevels 132a, 134a meet at an intersect 138a demarcating the respective planes at which the middle and tip bevels are formed. Adjacent middle and tip bevels 132b, 134b likewise meet at an intersect 138b. Tip bevels 134a, 134b meet at appointed apex 136 which first enters the skin of a patient (or sealing material associated with a fluid carrying vessel).

It has been surmised by the applicants herein and confirmed by the bench penetration tests discussed above that optimum results for reducing the height of intercepts 138a, 138b is achieved by forming primary bevel 130 and each of middle bevels 132a, 132b at angles of inclination 130Ω and 132Ω which are substantially equal if not identical. For instance, it has been found by applicants herein that optimum results are achieved by setting both inclination angles 130Ω and 132Ω, respective to imaginary plane 150, in a range of about 9 degrees ("°") plus or minus 1°. For purposes of simplicity, the transition demarcating primary bevel 130 from each of middle bevels 132a, 132b has been denoted by the numeral 131. It is surmised that by not varying the angle of inclination 132Ω for the middle bevels from angle of inclination 130Ω for the primary bevel, transition 131 demarcating primary bevel 130 from middle bevels 132a, 132b will be more rounded and less pronounced, contributing to a smoother, more continuous bevel face 140. Subsequent to formation of primary bevel 130, the hypodermic needle is rotated about the central axis 118 in both the clockwise and counterclockwise directions at rotational angle 132λ to form middle bevels 132a, 132b. It has been found by the applicants herein that optimum results are obtained when the range of rotational angle 132λ is about 8.5° plus or minus 5°.

Tip bevels 134a, 134b are likewise formed or otherwise provided on hypodermic needle 110 by inclining central axis 118 of hypodermic needle 110 to an angle 134Ω relative to reference plane 150, and by rotating the hypodermic needle about central axis 118 to an angle 134λ. It has been found by the applicants herein that optimum results for reducing the height of intercepts 138a, 138b demarcating the respective middle and tip bevels results when needle cannula 110 is inclined at an angle 134Ω in a range of about 15° plus or minus 2°, and when the needle cannula is rotated to an angle 134λ in a range measuring about 23° plus or minus 5°.

Figure 6:
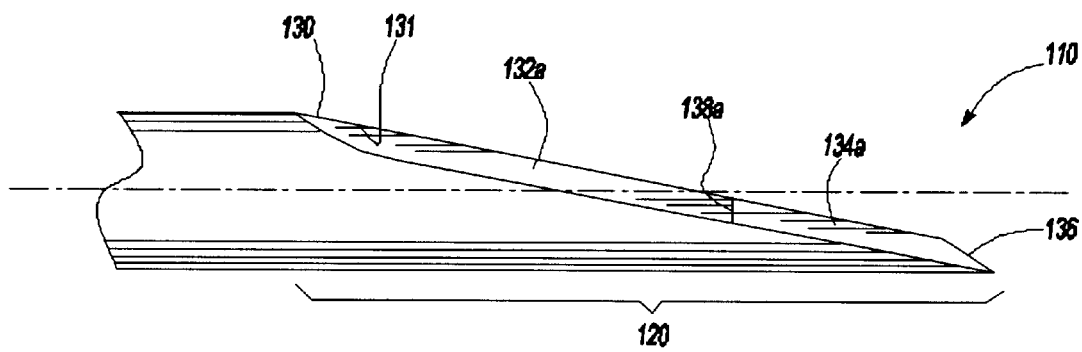
FIG. 6 is a side view of the multi-beveled needle tip of FIG. 4.
Figure 7:
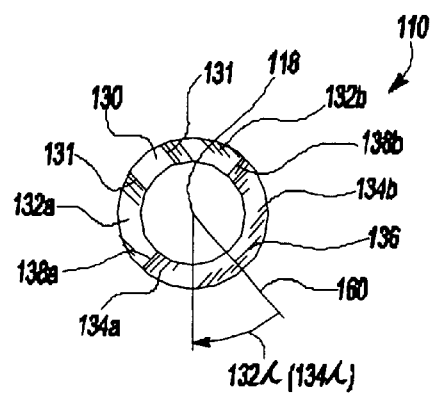
FIG. 7 is a front view of the multi-beveled needle tip of FIG. 4, depicting rotational angles about the central axis of the cannula for forming the multi-bevels and tip bevels.
Figure 8:
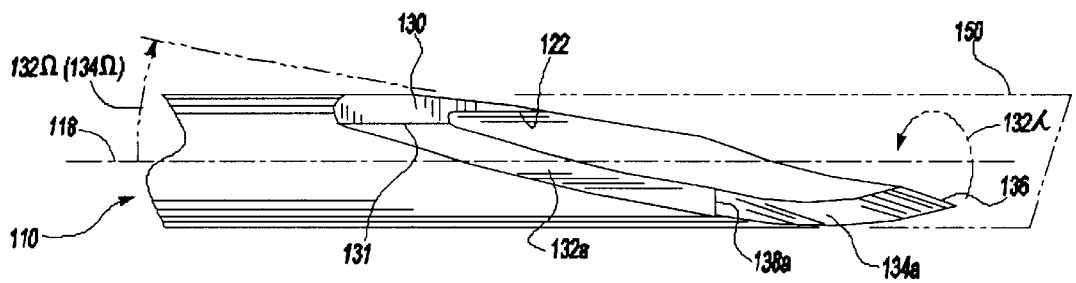
FIG. 8 is a second view of a multi-beveled needle cannula tip in accordance with the present invention, depicting the needle cannula rotated about the central axis at a first rotational angle and inclined at a planar angle with respect to an imaginary plane extending through the central axis for forming the middle bevels.
Figure 9:
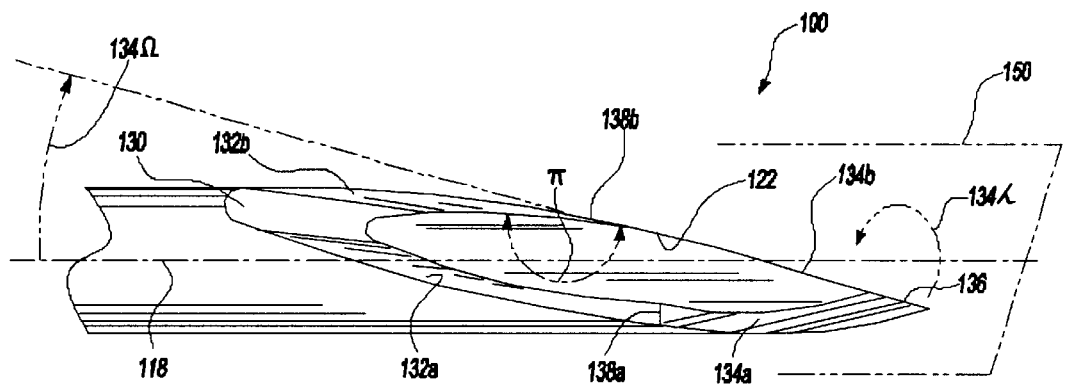
FIG. 9 is a third view of the multi-beveled needle tip in accordance with the present invention, depicting the needle cannula rotated at a second rotational angle about the central axis of the needle cannula and inclined at a second planar angle with respect to an imaginary plane extending through the central axis for forming the tip bevels.

FIG. 6 exemplifies the side profile of multi-beveled needle tip 120 formed in accordance with the present invention. Intercept 138a is reduced in height to an extent that when viewed from the side, middle bevel 132a and tip bevel 134a appear to provide a substantially-straight profile. The same effect can be seen in FIG. 9, where middle and tip bevels 132b, 134b, when viewed in side profile, define an angle "π" that is nearly 180° as measured about intercept 138b. The effect is a more continuous bevel face 140 free of abrupt intercepts 138a, 138b (or for that matter, transitions 131 demarcating the primary middle bevels), resulting in a needle tip requiring less penetration force. By reducing the heights of intercepts 138a, 138b, the effective outer diameter of needle point 120 is reduced, helping to reduce needle penetration forces.

The hypodermic needle 110 in accordance with the present invention can be formed from conventional materials such as steel or more preferably stainless steel. It will be realized by the skilled artisan that medical grade plastics, composites, ceramics, or like materials can be substituted.

The needle is preferably lubricated with various conventional lubricants such as silicone oils to enhance the effects obtained by applicant's geometry. The bevels can be formed on the hypodermic needle by conventional processes such as by grinding.

It will be evident to the skilled artisan that the bevels can be formed in any order desired. In one iteration, the primary and middle bevels can be formed before the tip bevels, in that in the preferred embodiment, the primary and middle bevels are formed at substantially identical angles of inclination 130Ω, 132Ω, and this might contribute to greater manufacturing efficiency. However, other manufacturing iterations can be employed. For instance, the tip bevels can be formed prior to manufacturing either of the middle or primary bevels. A further iteration would be to form the middle bevels 132a, 132b intermediate the steps required for forming primary bevel 130 and tip bevels 134a, 134b. For instance, the central axis of the hypodermic needle can be first inclined to angle 130Ω for formation of the primary bevel. Thereafter, the central axis of the hypodermic needle can be inclined to angle 134Ω, and thereafter rotated about central axis 118 to angles of rotation 134λ, for formation of the tip bevels. Thereafter, central axis of hypodermic needle 110 can be re-inclined to angle 132Ω, and rotated about central axis 118 to angles 132λ, for formation of the middle bevels. It will be realized by the skilled artisan that any order for forming the respective bevels for needle tip 120 that results in continuous bevel face 140 will achieve the advantages and results of the invention herein.

Tests were conducted comparing penetration force in rubber vial stoppers (20 millimeter rubber vial stoppers, model number 88-29530, manufactured by Abbott Laboratories of Ashland, Ohio) of 26 gauge needles produced in accordance with the above-identified steps against penetration forces exhibited by existing 26 gauge needles currently employed in HYPAK®-brand prefillable syringes, manufactured by Becton Dickinson Pharmaceutical Systems of Le Pont de Claix, France. Each of the needles were lubed with polydimethylsiloxane. Various angles of rotation 132λ, 134λ and angles of inclination 130Ω, 132Ω and 134Ω were tested. The resulting table illustrates that 26 gauge needles displaying needle point 120 according to the invention had significantly reduced needle penetration forces as compared to existing product:

26G 5-Bevel Needles
All needles lubed with polydimethylsiloxane
Rubber Vial Penetration Forces in Gram Force
(Average HYPAK Brand Needle Control Force = 468.5 gmf)

| Angle of Rotation | | Angle Of Inclination | | | |
|---|---|---|---|---|---|
| 132λ | 134λ | 130Ω, 132Ω | 134Ω | Point Length ("L") .094 | Point Length .080" |
| | | | | Tip Bevel Length .036" | Tip Bevel Length .040" |
| 35° | 35° | 10° | 10° | 341.5 gm.f | |
| 30° | 30° | 10° | 10° | 338.1 gm.f | |
| 22° | 22° | 10° | 16° | 344.5 gm.f | |
| 22° | 22° | 13° | 16° | 359.0 gm.f | |

The formation of a multi-beveled tip as described herein results in a bevel face 140 which is more continuous, free of abrupt intercepts or transitions. Absent abrupt intercepts or transitions, the likelihood that a portion of the bevel face will catch the skin or flesh or a patient is reduced, and the effective outside diameter of the needle point will be reduced, all meaning that needle penetration forces will be lessened.

Having described preferred embodiments of the syringe assembly including the improved needle shield and multi-beveled needle point, it will be understood by those skilled in this art that various modifications may be made within the purview of the appended claims. As described above, the method of making a sterilized syringe assembly of this invention, wherein the needle shield is formed of a styrene block thermoplastic elastomer, particularly a styrene block poly(ethylene/butylene) thermoplastic elastomer, has particular advantages for prefillable and prefilled syringes including improved needle sharpness, reduced perceived pain and it is believed that the improved needle shield will also reduce gas sterilization cycle time. The improved five-bevel needle configuration described herein may be utilized in combination with the improved needle shield to obtain superior results particularly with smaller needle gauges, such as 27 gauge needle cannulas or smaller. The syringe assembly of this invention may take additional forms particularly in regard to the injection device including the configuration of the barrel, the attachment of the needle cannula to the barrel and the plunger and stopper assembly, an embodiment of which is disclosed herein for illustration purposes only. Further, the configuration of the needle shield shown in FIGS. 1 to 3, may be modified as required for the application and preferably includes a rigid needle shield guard.

What is claimed is:

1. A syringe assembly, comprising:
   a syringe barrel;
   a needle cannula supported by said syringe barrel; and
   a needle shield having an open end and a needle passage through said open end configured to receive said needle cannula, and said needle cannula disposed thereon, wherein said needle shield is formed of a styrene block poly(ethylene/butylene) thermoplastic polymeric elastomer having a Shore A hardness of between 30 and 90.

2. The syringe assembly defined in claim 1, wherein said shield needle passage includes an internal annular rib adjacent said open end engaging a reduced diameter tip portion of said syringe barrel and reduce inadvertent removal of the shield from the syringe.

3. The syringe assembly defined in claim 1, wherein said styrene block poly(ethylene/butylene) thermoplastic elastomer has a shore A hardness of between 45 and 65.

4. The syringe assembly defined in claim 1, wherein said styrene block poly(ethylene/butylene) thermoplastic elastomer includes at about one to three percent of carbon black colorant.

5. The syringe assembly defined in claim 1, wherein said needle cannula is coated with a medical grade lubricant.

6. The syringe assembly defined in claim 5, wherein said medical grade lubricant is a silicone oil medical lubricant.

7. The syringe assembly defined in claim 1, wherein said syringe assembly is gas sterilized.

8. The syringe assembly defined in claim 7, wherein said syringe assembly is sterilized with an ethylene oxide gas.

9. The syringe assembly defined in claim 1, wherein said needle cannula includes a lumen therethrough defining a central axis, and a five-beveled point comprising a primary bevel, a pair of tipped bevels, and a pair of middle bevels intermediate said primary bevel and said tip bevels.

10. The syringe assembly defined in claim 1, wherein said needle cannula includes a lumen, a central axis therethrough and a five-beveled point at one end thereof, said five-beveled point comprised of a primary bevel, a pair of tip bevels and a pair of middle bevels intermediate said primary bevel and one of said pair of tip bevels, and each of said middle bevels being contiguous with said primary bevel and merging with a respective one of said tip bevels at an intersect, wherein the heights of the intercepts created between merging bevels is reduced resulting in a more continuous bevel face and a reduction in the penetration force to enter the flesh of a patient.

11. A syringe assembly, comprising:
    a generally tubular syringe barrel;
    a needle cannula supported by and extending from said syringe barrel including a lumen extending therethrough defining a central axis and a five-beveled point comprising a plurality of planar bevels extending at different angles of rotation relative to said central axis, including a primary bevel, a pair of tip bevels and a pair of middle bevels intermediate said primary bevel and said tip bevels; and
    a needle shield having an open end and a passage through said open end configured to receive said needle cannula and said needle cannula disposed therein, wherein said needle shield is formed of a styrene block thermoplastic elastomer having a Shore A hardness of between 30 and 90 and a gas permeability sufficiently high to permit gas sterilization through said needle shield.

12. The syringe assembly defined in claim 11, wherein said needle shield is formed of a styrene block poly(ethylene/butylene) thermoplastic elastomer.

13. The syringe assembly defined in claim 11, wherein said needle cannula is gas sterilized by ethylene oxide gas permeated through said needle shield.

14. The syringe assembly defined in claim 11, wherein said needle cannula is coated with a medical grade lubricant.

15. The syringe assembly defined in claim 11, wherein said shield needle passage includes an internal annular rib adjacent said open end engaging a reduced diameter tip portion of said syringe barrel to retain said needle shield to said syringe.

16. The syringe assembly defined in claim 12, wherein said styrene block poly(ethylene/butylene) thermoplastic elastomer has a shore A hardness of between 45 and 65.

17. The syringe assembly defined in claim 12, wherein said styrene block poly(ethylene/butylene) thermoplastic elastomer includes at least about one percent carbon black colorant.

18. The syringe assembly defined in claim 11, wherein said needle cannula includes a lumen, a central axis therethrough and a five-beveled point at one end thereof, said five-beveled point comprised of a primary bevel, a pair of tip bevels and a pair of middle bevels intermediate said primary bevel and one of said pair of tip bevels, and each of said middle bevels being contiguous with said primary bevel and merging with a respective one of said tip bevels at an intersect, wherein the heights of the intercepts created between merging bevels is reduced resulting in a more continuous bevel face and a reduction in the penetration force to enter the flesh of a patient.

19. A method of making a sterilized syringe assembly, comprising the following steps:
    forming a needle shield from a styrene block thermoplastic polymeric elastomer having a Shore A hardness of between 45 and 65 including a body portion including an open end and a passage extending through said open end configured to receive a needle cannula of a syringe;

assembling said needle shield on a needle cannula of a syringe; and immersing said syringe and needle shield assembly in a sterilization gas, said sterilization gas permeating said needle shield and sterilizing said needle cannula.

20. The method of making a sterilized syringe assembly as defined in claim 19, wherein said method further includes removing said sterilization gas from said needle shield passage by allowing said sterilization gas to permeate outwardly through said needle shield.

21. The method of making a sterilized syringe assembly as defined in claim 19, wherein said method includes forming said needle shield of a styrene block poly(ethylene/butylene) thermoplastic elastomer.

22. The method of making a sterilized syringe assembly defined in claim 19, wherein said method further includes coating said needle cannula with a medical grade lubricant prior to assembling said needle shield on said needle cannula.

23. A method of making a sterilized syringe assembly, comprising the following steps:

forming a needle shield having a body portion including an open end and a needle passage extending through said open end configured to closely receive a needle cannula of a syringe of a styrene block poly(ethylene/butylene) thermoplastic elastomer having a Shore A hardness of between 45 and 65;

assembling said needle shield on a needle cannula of a syringe; and immersing said syringe assembly in a sterilization gas, said sterilization gas permeating said needle shield and sterilizing said needle cannula.

24. The method of making a sterilized syringe assembly defined in claim 23, wherein said method further includes removing said syringe assembly from said sterilization gas and permitting said sterilization gas in said needle shield passage to permeate outwardly through said needle shield.

25. A method of preparing a syringe assembly to minimize penetration force necessary to insert a needle cannula of the syringe assembly into a patient, comprising the following steps:

forming a needle shield from a styrene block thermoplastic polymeric elastomer having a Shore A hardness of between 45 and 65 having a body portion including an open end and a passage extending through said open end configured to receive a needle cannula of a syringe; and, assembling said needle shield on a needle cannula of a syringe.

26. The method of preparing a syringe assembly as defined in claim 25, wherein said method includes forming said needle shield of a styrene block poly(ethylene/butylene) thermoplastic elastomer.

27. The method of preparing a syringe assembly defined in claim 25, wherein said method further includes coating said needle cannula with a medical grade lubricant prior to assembling said needle shield on said needle cannula.

* * * * *

UNITED STATES PATENT AND TRADEMARK OFFICE
CERTIFICATE OF CORRECTION

PATENT NO. : 6,629,963 B2
DATED : October 7, 2003
INVENTOR(S) : Prais et al.

Page 1 of 1

It is certified that error appears in the above-identified patent and that said Letters Patent is hereby corrected as shown below:

<u>Column 4,</u>
Line 7, delete "...block (polyethylene/butylene)..." and insert -- block poly (ethylene/butylene) --.

<u>Column 9,</u>
Line 16, delete "...clinical trial were..." and insert -- clinical trials were --.
Line 20, delete "...block (polyethylene/butylene)..." and insert -- block poly (ethylene/butylene) --.

<u>Column 10,</u>
Line 43, delete "...gracely scale, and integer..." and insert -- gracely scale, an integer --.

Signed and Sealed this

Sixteenth Day of March, 2004

JON W. DUDAS
*Acting Director of the United States Patent and Trademark Office*